(12) United States Patent
Seo et al.

(10) Patent No.: US 10,824,579 B2
(45) Date of Patent: Nov. 3, 2020

(54) NETWORK-ON-CHIP FOR NEUROLOGICAL DATA

(71) Applicant: Neuralink Corp., San Francisco, CA (US)

(72) Inventors: Dongjin Seo, San Francisco, CA (US); Paul A. Merolla, Redwood City, CA (US); Manuel Alejandro Monge Osorio, Redondo Beach, CA (US)

(73) Assignee: NEURALINK CORP., Fremont, CA (US)

( * ) Notice: Subject to any disclaimer, the term of this patent is extended or adjusted under 35 U.S.C. 154(b) by 0 days.

(21) Appl. No.: 16/354,059

(22) Filed: Mar. 14, 2019

(65) Prior Publication Data

US 2019/0286592 A1    Sep. 19, 2019

Related U.S. Application Data

(60) Provisional application No. 62/644,217, filed on Mar. 16, 2018.

(51) Int. Cl.
| | |
|---|---|
| *G06F 13/38* | (2006.01) |
| *G06N 3/06* | (2006.01) |
| *A61B 5/04* | (2006.01) |
| *G06N 3/063* | (2006.01) |

(52) U.S. Cl.
CPC .......... *G06F 13/38* (2013.01); *A61B 5/04001* (2013.01); *A61B 5/04004* (2013.01); *G06N 3/063* (2013.01); *G06F 2213/0038* (2013.01)

(58) Field of Classification Search
CPC .............. A61B 5/0478; A61B 5/04012; A61B 2562/125
See application file for complete search history.

(56) References Cited

U.S. PATENT DOCUMENTS

| | | | | |
|---|---|---|---|---|
| 2003/0198229 | A1* | 10/2003 | Ochi | H04L 12/2854 370/395.4 |
| 2007/0237495 | A1* | 10/2007 | Terada | G10L 19/005 386/343 |
| 2007/0265011 | A1* | 11/2007 | Han | H04B 17/327 455/437 |
| 2013/0230078 | A1* | 9/2013 | Chang | H04N 21/6143 375/147 |

(Continued)

FOREIGN PATENT DOCUMENTS

| | | |
|---|---|---|
| WO | 2015/066879 A1 | 5/2015 |
| WO | 2016/126340 A2 | 8/2016 |
| WO | 2018/102307 A1 | 6/2018 |

*Primary Examiner* — Getente A Yimer
(74) *Attorney, Agent, or Firm* — Kilpatrick Townsend & Stockton LLP (57) ABSTRACT

The embodiments disclosed herein relate to chips used to receive and process neurological events in brain matter as captured by electrodes. Such chips may include an array of amplifiers and electrodes to receive neurological voltage signals, the chip including a config circuitry in communication with the array of amplifiers and a controller, the config circuitry configured to receive program instructions and instruct the amplifiers of a voltage threshold and instruct the controller to pass on signals from only specific rows and columns of amplifiers, the controller in communication with the array of amplifiers, the controller configured to packetize the neurological voltage signals into data packets.

17 Claims, 6 Drawing Sheets

(56) References Cited

U.S. PATENT DOCUMENTS

| | | | | |
|---|---|---|---|---|
| 2014/0051373 A1* | 2/2014 | Klomsdorf | .......... | H04B 1/0475 |
| | | | | 455/114.3 |
| 2014/0057610 A1* | 2/2014 | Olincy | .................. | H04W 4/16 |
| | | | | 455/414.1 |
| 2014/0296678 A1* | 10/2014 | Mittal | ................. | A61B 5/0022 |
| | | | | 600/372 |
| 2015/0305643 A1* | 10/2015 | Negi | ................... | A61B 5/0478 |
| | | | | 600/378 |
| 2015/0326941 A1* | 11/2015 | Gao | ................ | H04N 21/43635 |
| | | | | 725/74 |
| 2018/0078767 A1 | 3/2018 | Rapoport et al. | | |
| 2018/0117309 A1 | 5/2018 | Rapoport et al. | | |

* cited by examiner

NETWORK-ON-CHIP FOR NEUROLOGICAL DATA

CROSS-REFERENCES TO RELATED APPLICATIONS

This application claims the benefit of U.S. Provisional Application No. 62/644,217, filed Mar. 16, 2018, which is incorporated by reference in its entirety for all purposes.

STATEMENT AS TO RIGHTS TO INVENTIONS MADE UNDER FEDERALLY SPONSORED RESEARCH AND DEVELOPMENT

NOT APPLICABLE

FIELD

This application relates to the field of computing devices, systems-on-chip, inter-chip networks, data packetizing, and data traffic flow.

BACKGROUND

Interfaces between living brain tissue and computer components have evolved over time. Certain interfaces allow electrodes into brain tissue to record neurological events. But recording such data, packetizing it, and processing it can be difficult, if the number of electrodes is more than just a few. Some examples include the "sewing machine" arrangement of electrode placement as described in International Patent Application No. PCT/US2015/066879, published as WO 2016/126340 and hereby incorporated by reference.

BRIEF SUMMARY

System and methods here may include using a chip with an array of amplifiers and electrodes to receive neurological voltage signals, the chip including a config circuitry in communication with the array of amplifiers and a controller, the config circuitry configured to, receive program instructions and instruct the amplifiers of a voltage threshold and instruct the controller to pass on signals from only specific rows and columns of amplifiers, the controller in communication with the array of amplifiers, the controller configured to packetize the neurological voltage signals into data packets. In some example embodiments, the data packets are variable in length depending on the number of amplifiers instructed by the controller to be passed on. In some examples, the systems and methods further include a merge circuitry on the chip, configured to receive the data packets from the controller and pass the packetized voltage signals off the chip.

In some example embodiments, an analog-to-digital converter is configured between the array of amplifiers and the controller, the analog-to-digital converter configured to convert analog signals from the array of amplifiers to digital signals, and the controller further configured to instruct the analog-to-digital converter to pass only signals from certain rows of amplifiers in the array of amplifiers. In some example embodiments, a multiplexer is configured between the analog-to-digital converter and the controller, the multiplexer configured to serialize the digitized amplified neurological voltage signals and pass the serialized digitized amplified neurological voltage signals to the controller, and the controller further configured to instruct the multiplexer to pass only signals from certain columns of amplifiers in the array of amplifiers. In some examples, the config circuitry is in communication with the controller, the config circuitry configured to receive program instructions and instruct the controller to pass data packets to either the merge circuitry or a compression engine. In some examples, the config circuitry is further configured to instruct the compression engine to send summary data to the merge circuitry. In some examples, the compression engine is configured to compress data packets from the controller and pass the compressed data packets to the merge circuitry. In some examples, the merge circuitry is configured to pass data packets to a second chip, in communication with the chip in serial. In some examples, the merge circuitry passes data packets to the second chip through a serializer queue. And in some examples, the instruct the amplifiers of a voltage threshold is individualized for specific amplifiers in the array of amplifiers.

Additionally or alternatively, example embodiments here include a method, comprising, receiving neurological voltage signals at an array of amplifiers on a chip, the neurological voltage signals received through at least one electrode, sending instructions by a config circuitry on the chip, to a controller on the chip, the instructions including instructions to pass on signals from only specific columns and rows of amplifiers in the amplifier array, packetizing, at the controller, the passed on signals from the array of amplifiers, wherein the data packets are variable in length depending on the number of amplifiers passing on signals, and passing the data packets off the chip, by a merge circuitry, the merge circuitry in communication with the controller and a compression engine. In some examples, converting, by an analog-to-digital controller, the neurological voltage signals to digital signals, and instructing the analog-to-digital converter, by the controller, to pass only signals from certain rows of amplifiers in the array of amplifiers. In some examples, receiving, by the config circuitry, program instructions, sending instruction, by the config circuitry, to the controller, to send packets to either the merge circuitry or a compression engine. In some examples, sending instruction, by the config circuitry, to the compression engine to send summary data to the merge circuitry.

Additionally or alternatively, in some examples, compressing data packets, by the compression engine and passing the compressed data packets to the merge circuitry. In some examples, passing, by the merge circuitry, data packets to a second chip, in communication with the chip in serial. In some examples the passing, by the merge circuitry, of data packets to the second chip is through a serializer queue.

Additionally or alternatively, some examples include non-transitory computer readable media for a method of handling data, the method comprising, receiving neurological voltage signals at an array of amplifiers on a chip, the neurological voltage signals received through at least one electrode, sending instructions by a config circuitry on the chip, to a controller on the chip, the instructions including instructions to pass on signals from only specific columns and rows of amplifiers in the amplifier array, packetizing, at the controller, the passed on signals from the array of amplifiers, wherein the data packets are variable in length depending on the number of amplifiers passing on signals, and passing the data packets off the chip, by a merge circuitry, the merge circuitry in communication with the controller and a compression engine. Some example further comprising, receiving, by the config circuitry, program instructions, sending instruction, by the config circuitry, to the controller, to send packets to either the merge circuitry or a compression engine. Additionally or alternatively, some examples further comprising, sending instruction, by the config circuitry, to the compression engine to send summary data to the merge circuitry. Some examples further comprising, compressing data packets, by the compression engine and passing the compressed data packets to the merge circuitry.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION

Reference will now be made in detail to embodiments, examples of which are illustrated in the accompanying drawings. In the following detailed description, numerous specific details are set forth in order to provide a sufficient understanding of the subject matter presented herein. But it will be apparent to one of ordinary skill in the art that the subject matter may be practiced without these specific details. Moreover, the particular embodiments described herein are provided by way of example and should not be used to limit the scope of the invention to these particular embodiments. In other instances, well-known data structures, timing protocols, software operations, procedures, and components have not been described in detail so as not to unnecessarily obscure aspects of the embodiments of the invention.

Overview

Brain interfaces with computer systems may require the use of electrodes to receive neurological impulses and turn them into voltage readings or signals. Some example solutions utilize electrodes that contact the outside of the brain or rest on the outside of the skull. Some example solutions utilize electrodes implanted into brain tissue itself. In any arrangement, it may be useful to utilize many different electrodes, placed all over a brain, in order to cover as much of the brain as possible to sense as many neurological readings as possible. There is a need for reliable communication from such electrodes to a computer system for analysis of neurological readings In some example arrangements, electrodes are arranged on a strand or lead and connect to an independent computer chip. The electrodes sense neurological impulses as voltage signals, and pass that information to the chips which handle the data. In one example embodiment described below, such chips are customized application specific integrated circuit (ASIC) chips which are connected to a strand or strands with electrodes attached to them. These ASIC chips may be referred to as a SoC (system-on-chip) with their own ROM, RAM, EEPROM, flash memory, etc.

These customized ASIC chips may receive, amplify, digitize, and process the voltage readings of the electrodes sensing the neuron signals into data packets for data processing. The chips may then pass the packets along the chip network to ensure each chip sends data on time and send data packets to signal processing on a pin grid array (PGA) board and streamed off to another computing system for analysis and storage.

But as each chip may only be configured to communicate with a limited number of electrodes, and many multiple electrodes may be needed for coverage of a brain, multiple chips may be used to handle all of the signals from all of the electrodes. Such a network of chips may communicate with one another and pass packets of data along before offloading from an intra-chip network to another computing system In some examples, chips are arranged in a linear network as in series. In some examples, chips are arranged in multi-dimensional arrangements such as a two dimensional array. Other arrangements are possible as well alternatively or additionally.

Multi-Chip Network Examples

Figure 1A:
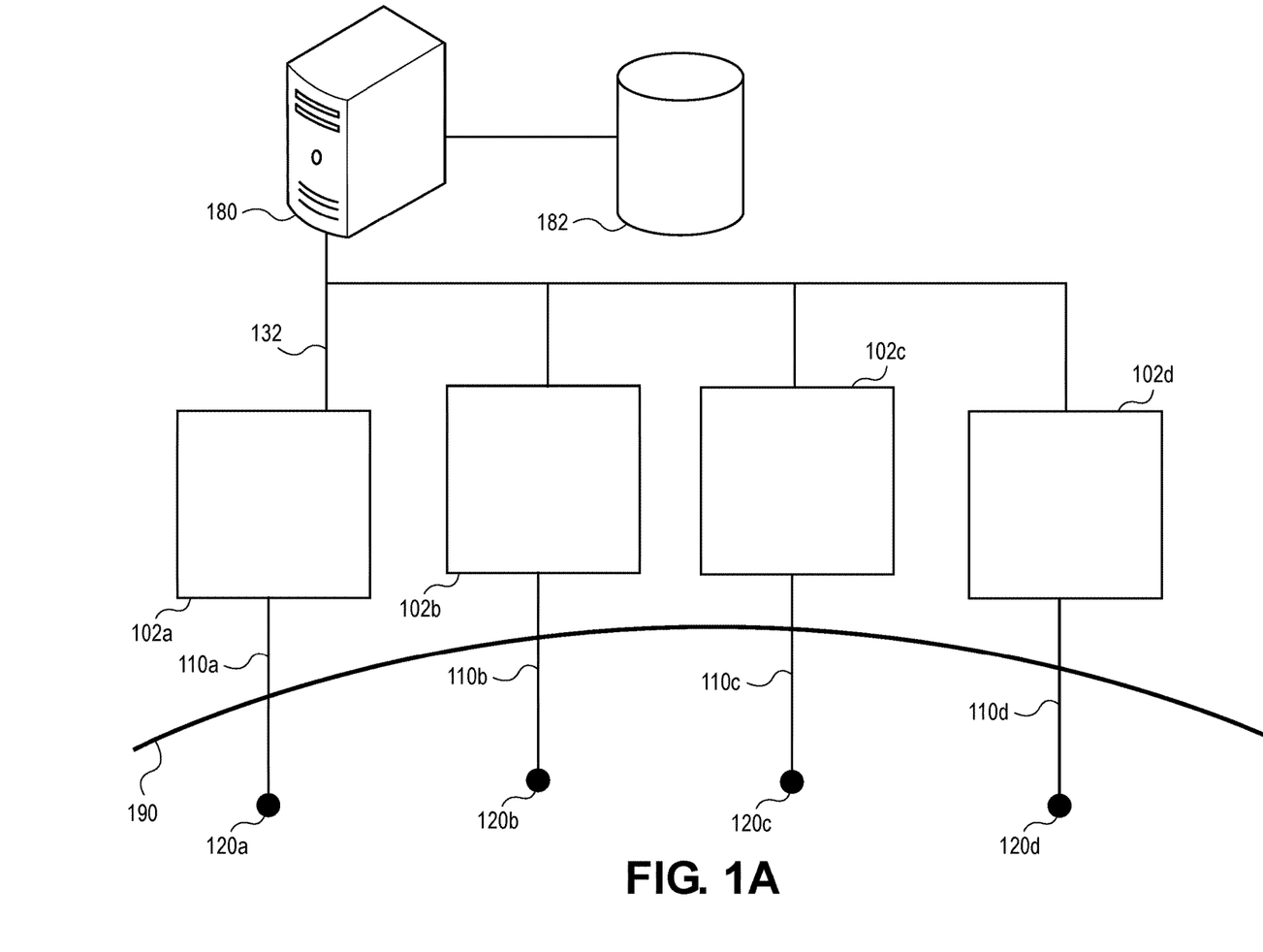
FIG. 1A is an example multi-chip architecture used to implement the embodiments described herein.

FIG. 1A shows an example network of multiple chips 102a-d, each receiving signals from a subject brain 190, through electrodes 120a-d on separate leads 110a-d. In some examples, these chips 102a-d may digitize, process, and/or packetize neurological readings before sending signal data off the chip 132 to a back end computing system 180 and/or data storage 182. The back end computing system 180, 182 may receive, store, further process and analyze the data from the electrodes 120a-d of the neurological signals.

The example of FIG. 1A shows an example with four chips 102a-d, each with its own leads 110a-d, and its own electrodes 120a-d. These are only simplified examples and not intended to be limiting. Many multiple numbers of chips may be used to cover a brain hemisphere or brain. For example, ASIC chips may be arranged in series with 80 chips per brain hemisphere, for a total of 160 chips per brain. In some examples, each chip may include 2 mm×2 mm bare die bonding for 64 channels/electrodes. In some examples, each chip 102a-d may include 256 channels. In some examples, 10,240 electrodes 120a-d may be implanted into a brain 190 for sensing neurological signals.

Linear Network Examples

Figure 1B:
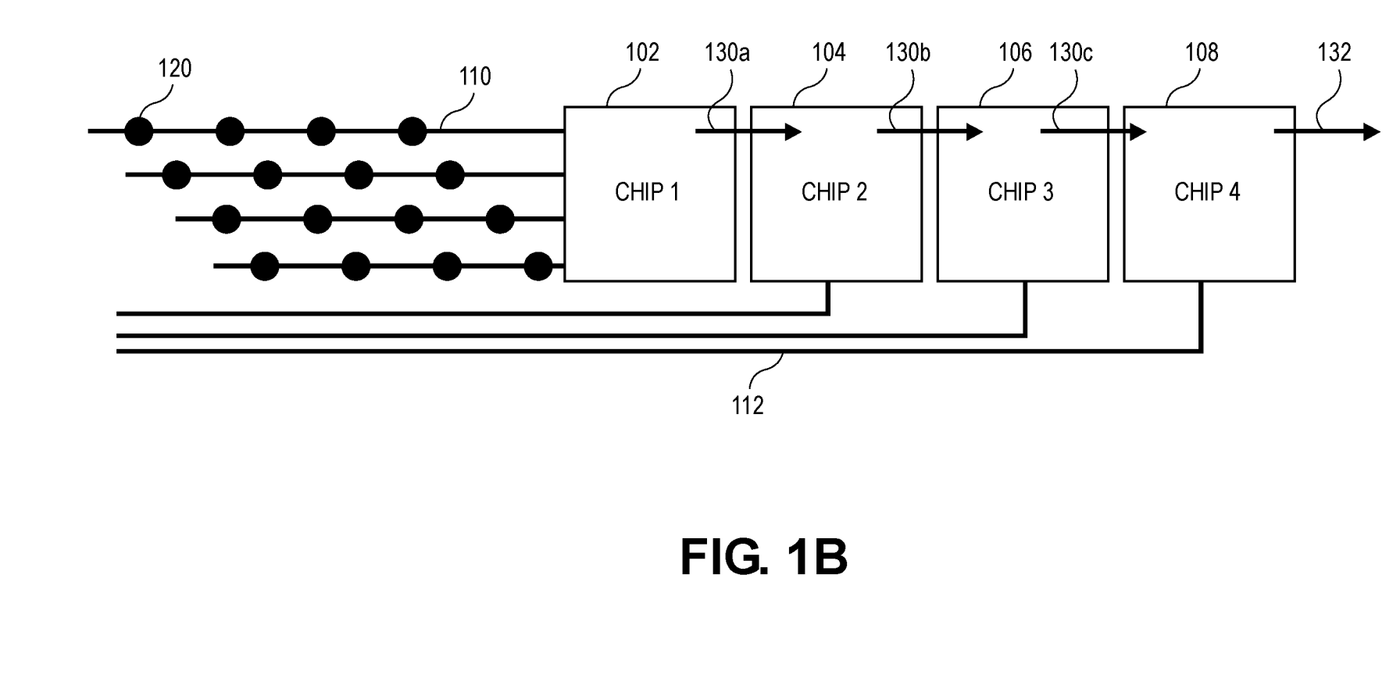
FIG. 1B is an example linear chip architecture used to implement the embodiments described herein.

FIG. 1B is a diagram showing an architecture diagram of a serial arrangement of multiple chips in a chip-to-chip network. Instead of a single chip as shown in FIG. 1A, in FIG. 1B, four chips 102, 104, 106, 108 are arranged in series before offloading their signal data to a back end computing system (180, 182 in FIG. 1A). In the example of FIG. 1B, each chip 102, 104, 106, 108, has its own lead 110, 112 etc. or set of leads with multiple electrodes 120 arranged on each lead. Although not depicted in FIG. 1B, each chip would have its own electrodes and leads as shown for Chip 1 in the figure. The example shows four electrodes 120 on each of four leads 110 per chip 102 but this is merely an example. Any number of electrodes 120 could be configured on any number of leads 110 per chip 102. For example, each lead 110 may include eight electrodes 120. For example, each chip could include eight leads 110. In such examples, with eight electrodes and eight leads, 64 channels or inputs may be arranged per chip.

As shown below, each chip 102 may then include an eight-by-eight grid of amplifiers to receive and process these signals as described herein. In such examples, a four chip network may include a total of 256 electrodes and the same number of amplifiers, 64 per chip. In some examples, more chips may be configured in series, for example, sixteen chips may be configured in series. In some examples, eight chips may be configured in series. Any of various number of chips could be networked together as described herein.

The example of FIG. 1B also shows four chips 102, 104, 106, 108 connected in series by way of a communication lines 130a-c with one another in an intra-chip network. Since the chips 102, 104, 106, 108 are connected by communication lines 130a-c in series, any data such as packetized signal data generated on each chip may need to be passed on to the next chip, and the next chip, in series in order to pass the data off the chip sets 132 to a computer or other system to process and store the data (180, 182 in FIG. 1A).

It should be noted that the example of FIG. 1B is a one dimensional or linear network arrangement for example purposes only. The system could be arranged with a two dimensional arrangement with chips connected to more than one other chip in series, but to a grid of other chips in a similar or same way they are connected in the one dimensional arrangement as shown in FIG. 1B. In such examples, each chip could be similarly programmed as described here, to send packets to a chip above, below, or to the side of it in a grid or other multi-dimensional arrangement, as well as or in addition to the linear arrangement depicted in FIG. 1B. The number of four chips in the example is also not intended to be limiting. Eight chips, or sixteen chips or more could be arranged in a similar fashion. Any number of chips could be arranged similarly.

In the example of FIG. 1B, each electrode 120 senses neurological voltage readings, and passes a voltage signal to its respective amplifier within its respective chip 102. The chip 102 receives these electrode 120 signals and processes them as described herein, and passes packets representing data from the received signals to the next chip 104, which also receives its own electrodes' signals as well as those packets passed from the previous chip 102. The second chip 104 likewise passes not only its own packets of processed signals as described herein, but also the packets it received from the previous chips 102 to the third chip 106. Thus, this third chip 106 receives from the second chip 104, packets from the first two chips 102, 104, and creates packets from the signals it receives from its own respective electrodes, and passes those as packets to the fourth chip 108. This final fourth chip 108 sends on to a computer for processing and/or storage, the packets it has received from the previous three chips 102, 104, 106 but also the packets it creates from the signals generated by its respective electrodes.

As can be seen from this kind of serial packet passing arrangement, depending on how many signals are being processed from the various electrodes 120, packet management may be required to deal with and efficiently pass packet data for processing.

Chip Architecture Examples—Signal Data Flow

Figure 2:
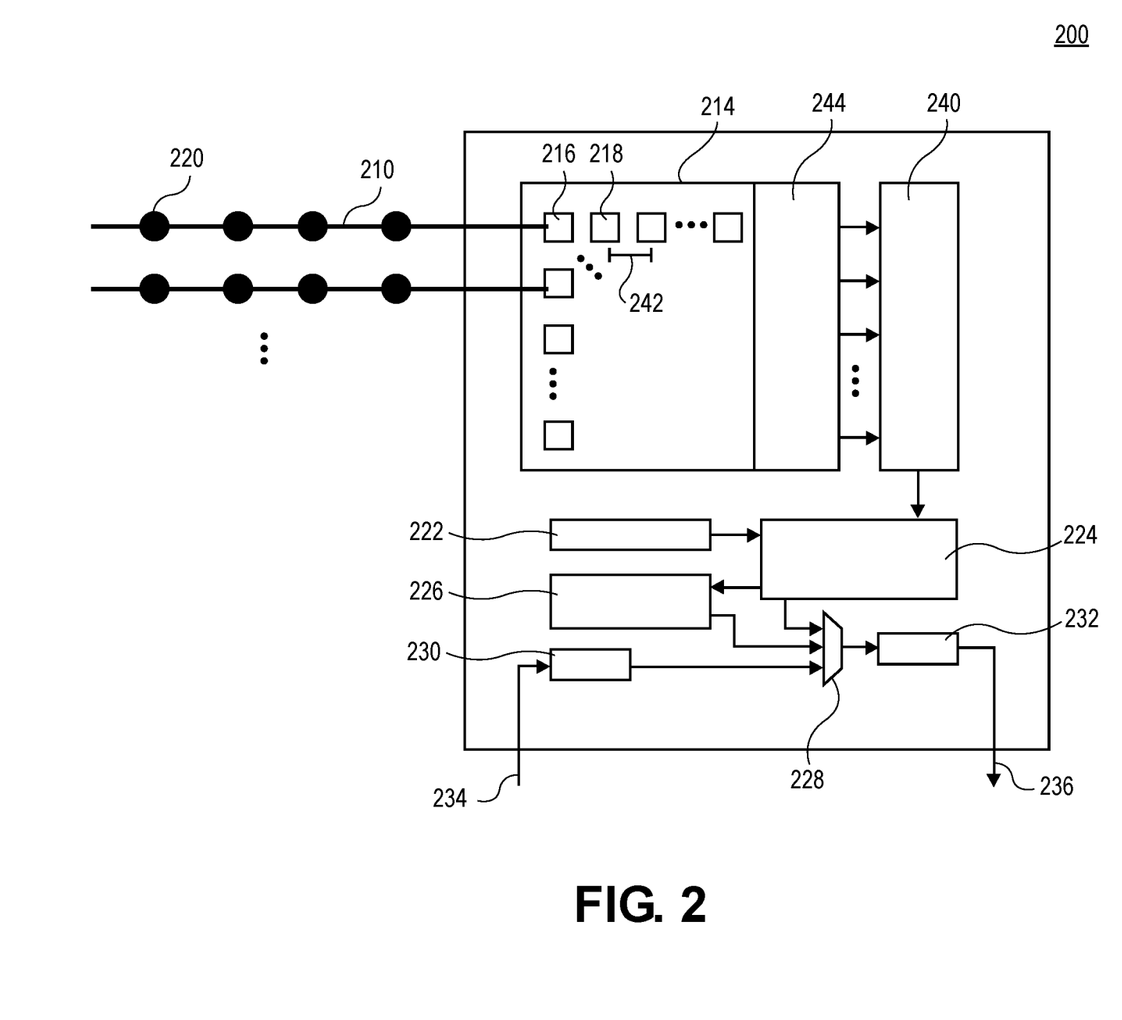
FIG. 2 is an example chip architecture and data flow used to implement the embodiments described herein.

FIG. 2 shows an example ASIC chip 200 architecture with the flow of signal data within one chip 200. The chip 200 in FIG. 2 is just one of the four chips (102, 104, 106, 108) shown in the example of FIG. 1B. The chip 200 in FIG. 2 can include one input 234 from previous chip in series (e.g. Li port for Left in), if there is one, and one output 236 (e.g. Ro port for right out) to the next chip in series if there is one, and/or to another computing device for data analysis, storage, etc. as shown as 130a-c in FIG. 1B. This main input 234 and output 236 is for packetized inter-chip data transfer.

Components of chip 200 include an array of amplifiers 214, an analog-to-digital converter 244, a multiplexer 240, a controller 224, a configuration ("config") circuitry 222, a compression engine 226, a merge circuitry 228, a deserializer 230, and a serializer 232. It should be known that the circuitry described in the various chip 200 elements herein may be hardware implemented using any number of resistors, capacitors, diodes, leads, busses, memory, ROM, processors, or any other kind of discrete hardware components. In some examples, additionally or alternatively, the circuitry described could be virtualized in a cohesive processor and memory and run as software. Either option may be utilized alone or in combination with each other, although the components described herein are referred to as hardware elements of circuitry. In some examples, the config circuitry is a processor or a digital signal processor.

In some examples, a deserializer 230 on the chip 200 may convert packets from an off chip serial link to an on-chip network as well as act as a queue for incoming data packets from the input 234. In some examples, a serializer 232 may act as a queue for outbound packets to be sent to other chips 236 or off chip to another computing resource. In some examples, these queues 230, 232 are de-coupled and independent and can send/receive/queue without effect on one another. The various ways that the merge circuitry 228 between the deserializer 230 and serializer 232 to merge data packets is described later herein.

Data flow within the chip begins upon providing power to the chip 200. These electrodes 220 detect neuron voltage readings within or from the brain itself and pass on the analog voltage signals to the chip 200 by way of individual amplifiers 216, 218. In the example, the amplifiers are arranged in an array of amplifiers 214, each in communication with a lead 210 and thereby any number of electrodes 220 as shown in FIG. 1B as a one-to-one ratio, with one amplifier for each electrode 220. In some examples, the array of amplifiers 214 is arranged in a grid of eight rows by eight columns. In some examples, the arrays of amplifiers are arranged differently or with a different number of amplifiers 216, 218. The example of sixty-four total arrayed amplifiers 214 in an eight-by-eight grid is not intended to be limiting, but merely an example. In some examples, these amplifiers 216, 218 within the array of amplifiers 214 are similarly arranged on the chip 200 at a spacing 242 of 180 μm, in both a horizontal and/or vertical dimension. In some examples, the spacing of these amplifiers 216, 218 is larger or smaller than 180 μm, and this dimension is only given as an example. In some examples, the amplifiers 216, 218 are similarly spaced between 150 μm and 200 μm from one another, both vertically and/or horizontally.

This array of amplifiers 214 are configured on the chip 200 to receive analog signal information from the electrodes 220 through a lead 210 and then amplify the signals. These amplified analog signals are then sent to an analog-to-digital converter 244 which digitizes the signals from the analog array of amplifiers 214. The analog-to-digital converter then sends the digitized signals to a multiplexer 240 for serializing the signals and/or data. In the example of the figure, there are eight analog-to-digital converters that receive signals from each of the eight rows of amplifiers 216. In some examples, the multiplexer 240 may be configured to select data from all of the rows of amplifiers 216 to build data packets. In some examples, additionally or alternatively, the multiplexer 240 may be configured to select only certain rows of amplifiers in the array of amplifiers 214 at a time to build packets more easily, for example one row at a time. In some examples, the multiplexer 240 may be configured to sample different rows of amplifiers in the array of amplifiers 214 at different times to build data packets. Such selection of amplifiers to include or not include in a data packet may be instructed from the config circuitry 222, which can be programmed through scan chain or a JTAG interface to enable a desired mode, and instruct the controller 224 as described below and in FIG. 3.

The config circuitry 222 is the primary programming interface to the chip from the back end computing system (element 180 in FIG. 1), that can configure the system to operate in the desired mode (as discussed herein, for example, skip channel, scheduled column, event voltage spikes, etc.). As the remaining circuitry are unique instruments in the orchestra playing specific roles, the config circuitry 222 is the conductor.

As data is serialized in the multiplexer 240, the serialized data information signals are sent to a controller 224 which is in communication with a compression engine 226 and a merge circuitry 228. The controller 224 creates data packets with the various digitized electrode signal data as described above and in FIG. 3. Thus, based on the settings/mode set by the config circuitry 222, the controller 224 is the main circuitry that packetizes the data and sends data to the next set of stages/circuitry as described herein. Also shown in the example chip 200 of FIG. 2 is a config circuitry 222 and a compression engine 226 as well as the merge circuitry 228, all in communication with the controller 224.

In some examples, the signals are compressed by the compression engine 226 as described herein, but in other examples, they are sent straight to the merge circuitry 288 without compression. The merge circuitry 228 is arranged to receive data packets from three sources, the controller 224, the compression engine 226 and the de-serializer 230. The merge circuitry 228 is configured to and/or programmed to decide which packets to send off chip and when to send those packets, based on its programming. The merge circuitry 228 sends packets off chip through a serializer 232 out to the next chip 236 or computing device as described herein.

In some example implementations, compression may occur in the compression engine 226, not at the array of amplifiers 214. In such examples, all of the raw, high-bandwidth signals (e.g. 20 kHz sampling) from the array of amplifiers 214 are sent to the compression circuitry 226 by way of the controller 224. In some examples, raw data may be unprocessed data and high-bandwidth signals may be data containing low and high frequency contents of neurological signals. In such examples, algorithms (e.g. Non-linear Energy Operator, or "NEO") may be used to detect voltage spikes, and thereby select certain signals over a threshold to process and certain signals below the threshold to discard. In some examples, a voltage spike is a detected voltage that is higher than a predetermined threshold. Thus, thresholds that determine whether a voltage spike is analyzed or not, may be set by the config circuitry 222.

In some example implementations, alternatively or additionally, data compression may occur directly on the array of amplifiers 214, to limit what signals are sent from the amplifiers 216 at the source. In such examples, thresholds may be set and only signals exceeding the threshold are sent to the controller circuitry 224 so it does not need to deal with all high-bandwidth data but only receives event signals that exceed a threshold.

Chip Architecture Examples—Instruction and Non-Signal Flow

Figure 3:
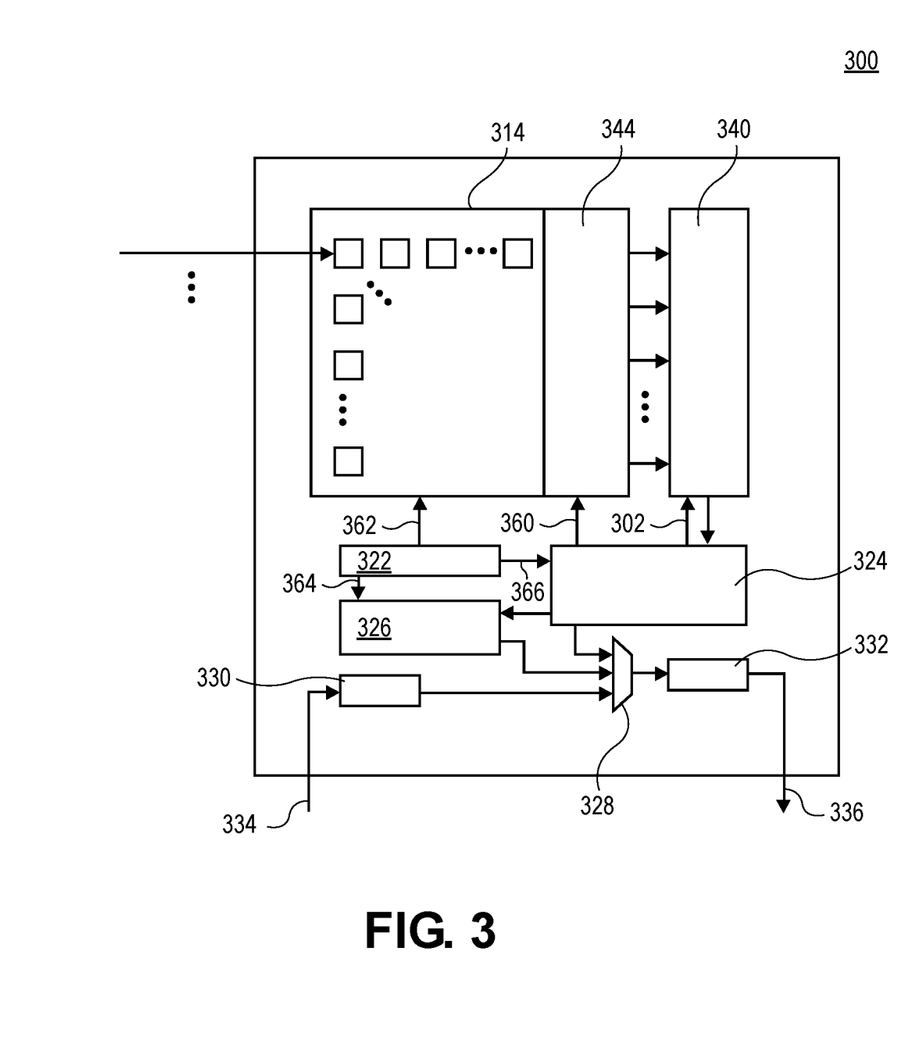
FIG. 3 is another example chip architecture and signal flow used to implement the embodiments described herein.

FIG. 3 shows an example of programming instruction and non-signal flow, such as program or instruction flow, within the ASIC chip 300.

Components of chip 300 include an array of amplifiers 314, an analog-to-digital converter 344, a multiplexer 340, a controller 324, a configuration ("config") circuitry 322, a compression engine 326, a merge circuitry 328, a deserializer 330, and a serializer 332. Such programming may be sent before the chip 300 is put into use, and/or updated while the chip 300 is in use as described below. The programming may affect how the chip 300 handles signal data and data packets.

In the example of FIG. 3, a config circuitry 322 may be programmed before the chip 300 is booted to instruct the various component parts regarding handling of signal data and data packets. A scan chain path may be used to send the config circuitry 322 and/or controller 324 program instructions. The config circuitry 322 then sets all the parameters for the chip, including, amplifier settings, number of amplifiers to read out, compression engine thresholds, etc. For example, a chip may start streaming data upon getting powered on with parameters that are preset in this way. The config circuitry 322 may then store the program instruction and, for example, instruct 362 the array of amplifiers 314 which run mode is being used at a particular time, as well as send the compression engine 326 instructions 364 regarding parameters for compression. The config circuitry 322 may also send communications 366 to the controller 324 as described below.

The compression engine 326 may also be programmed to take raw data passed from the analog-to-digital converter 344 and send compressed streams of data such as summary statistics, voltage spike detection, and/or other event based triggers off the chip 300.

In some examples, the compression engine may detect and send voltage spike data based on pre-determined threshold set by the config circuitry to reduce the data bandwidth. In some examples, the reduction in bandwidth is up to, or exceeding 1,000 times less data. In some example implementations, this may reduce bandwidth by using, for example, lossless compression like PNG, TIFF, and/or ZIP. Additionally or alternatively, examples may reduce bandwidth by only sending high-fidelity signals around voltage spike events. Additionally or alternatively, examples may reduce bandwidth by utilizing voltage spike timing data. Additionally or alternatively, examples may reduce bandwidth by using local field potential data.

In the example of FIG. 3, the config circuitry 322 may be programmed in many various ways to configure various components, such as but not limited to polling frequency of electrodes by way of the array of amplifiers 314, throttling arrangements to include and/or excluding signals to pass on, row and/or column selection of amplifiers in the array of amplifiers 314 for data polling, defining voltage thresholds for electrode event decision making by the compression engine 326, and many other decisions for signal and/or data handling. The controller 324 may orchestrate the analog-to-digital conversion 344, by communication 360. Such communication 360 may include instruction as to which columns of the amplifier in the array of amplifiers 314 should be sampled when. The controller 324 may instruct the amplifier 314 to skip columns and not pass on any data from those amplifier columns. In some examples, sampling rates and/or times may be varied as well. For example, 20 kHz may be set as a sampling rate at one time, but every other time may be set lower, or skipped altogether. Lower sampling rates from each channel/amplifier may also reduce the amount of data packets generated.

In some examples, a typical controller 324 instruction is to every 6.25 µs (160 kHz) digitize by the ADC and its 80 bits (8 rows×10 bits) are locally stored. Depending on the chip configuration, this data is packetized and sent off to multiple streams, high bandwidth and compression.

As shown in FIG. 3, the controller 324 and/or compression engine 322 may be programmed to select signals only from particular rows and columns of amplifiers in the array of amplifiers 314 to throttle the amount of data being generated by each chip 300. This decision can be created on an amplifier-by-amplifier granular level, as well as row based, and/or column based sampling decisions as well as any kind of combination of the above. The controller 324 may then build data packets based on a mode set passed on from the config circuitry 322.

The controller 324 may also communicate to the multiplexer 340 and instruct the multiplexer 340 as to which row of amplifiers in the array of amplifiers 314 to select to serialize. The controller 324 may only capture signals from a particular column at a particular time interval. In such an arrangement, certain columns are assigned to time slices and only signals generated by those electrodes, through those amplifiers, at that time are captured, to create sub-sampling of amplifiers in a customized way for each separate amplifier, and/or rows of amplifiers, and/or columns of amplifiers. Programmable sampling in this way may throttle the amount of signal data being generated per chip, and be included in the variable packet arrangement as described herein.

Another example of data packet handle may include instructions as to whether to pass packets from the controller 324 to the compression engine 326 or to the merge circuitry 328 directly.

Data Packet Handling Examples

The network may be programmed with a concept of backpressure. As packets are queued, the de-serializer 332 may stall packets being sent by the merge circuitry 328 in order to send data packets to fill the available bandwidth. Such packets may be placed in buffers (for example, a store and forward buffer) to await passing. Meanwhile, the system is able to report how many packets are being stored in which buffers, and that information may be used as a sense of back pressure. At some predetermined amount of back pressure, a back log of data packets may cause the merge circuitry 328 to drop data packets, due to lack of bandwidth. For example, if the controller 324 determines that there is no room in any of the queues, it may order a packet be dropped from the merge circuitry 328. In such examples, a signal may be sent off chip that a packet was dropped.

Event Driven Examples Using Thresholds

One example of deciding which received neurological signals to process, is to set a threshold, as discussed, and only handle signals that are indicative of a particular type of neurological event in the brain. In such examples, instead of polling each electrode a certain number of times a second, for sensed voltage signals, only signals that pass a certain preset threshold are considered worthy of handling, for example, those signals associated with a neuron firing. Such examples may reduce the amount of data being generated, because the sheer number of signals being analyzed is reduced from a full time polling scenario. For example, polling 20,000 times per second for each channel, to make sure every event is captured, may require a great deal of bandwidth, but, neurological events that produce a signal over a particular preset voltage threshold, may only occur a few times per second, in some examples, less than ten times per second. The result is that a threshold which only captures neurological events creates a scenario with magnitudes fewer signals to handle than a constant polling scenario.

As such, only neurological events that are shown to exceed a pre-determined voltage threshold may be captured. In such examples, voltage spikes, captured by the electrodes may be processed, packetized and sent along, whereas non-events or voltage readings that did not exceed a previously established threshold, would not be processed. Such a defined voltage threshold can be programmed by the config circuitry 322 by instruction 364 to the compression engine 326 of a specific threshold that must be met. Algorithms, such as Non-linear Energy Optimization, or other algorithm, may be used to look for a large deflection in signal data.

In some examples, the chips may be programmed to mix both full bandwidth polling, and event driven threshold data handling. In such examples, high bandwidth polling may occur until a certain amount of programmed bandwidth is consumed, and then the rest of the bandwidth is dedicated to event driven signal processing.

In some examples, a refractory period may pause the system for a set time, for example, a few milliseconds after an event is detected, in order to reduce the chances or eliminate the threat of data congestion. Additionally, neurons in the brain take a certain amount of time to spike or peak after they each fire once. Because of this, built in rest periods also limit the signal flow.

Variable Packet Examples

Although data paths on chip may have the ability to handle high bandwidth, passing data packets from chip-to-chip or to another computing resource may have lower or limited bandwidth available for use. Also, in fixed schedule examples, the amount of data generated by each chip is more easily predicted, because that amount of data is programmed. But in event driven examples, it may be harder or not possible to predict when data is going to be generated, because the events are caused by neurons in the brain. Thus, a variable packet arrangement may be useful for event driven situations, but not necessarily exclusively.

Thus, it may be beneficial to better manage what data is sent between chips and off chip. In such circumstances, users may select/program which high bandwidth data to send off chip. As discussed, the controller may be programmed to only instruct the amplifier array or multiplexer to send signal data for some, not all of the amplifiers at a given time for packetization. In some examples, the different rows and/or the different columns of amplifiers may be selected by the controller to sample and then packetize. In such examples, packets may be different lengths due to the different number of amplifier data which is packetized in a given packet. This may result in packets of different lengths, not a standard length with a payload full of null data sets, but instead tailored to what is on each data packet. Also, the structure of each packet may be minimized for efficiency purposes. In certain example embodiments, packets may be customized, varied, and/or sized according to the particular data that each needs to encapsulate and sent on for a given program or scenario. In such a way, empty packets and/or wasted bandwidth may be minimized, thereby relieving congestion.

Figure 4:
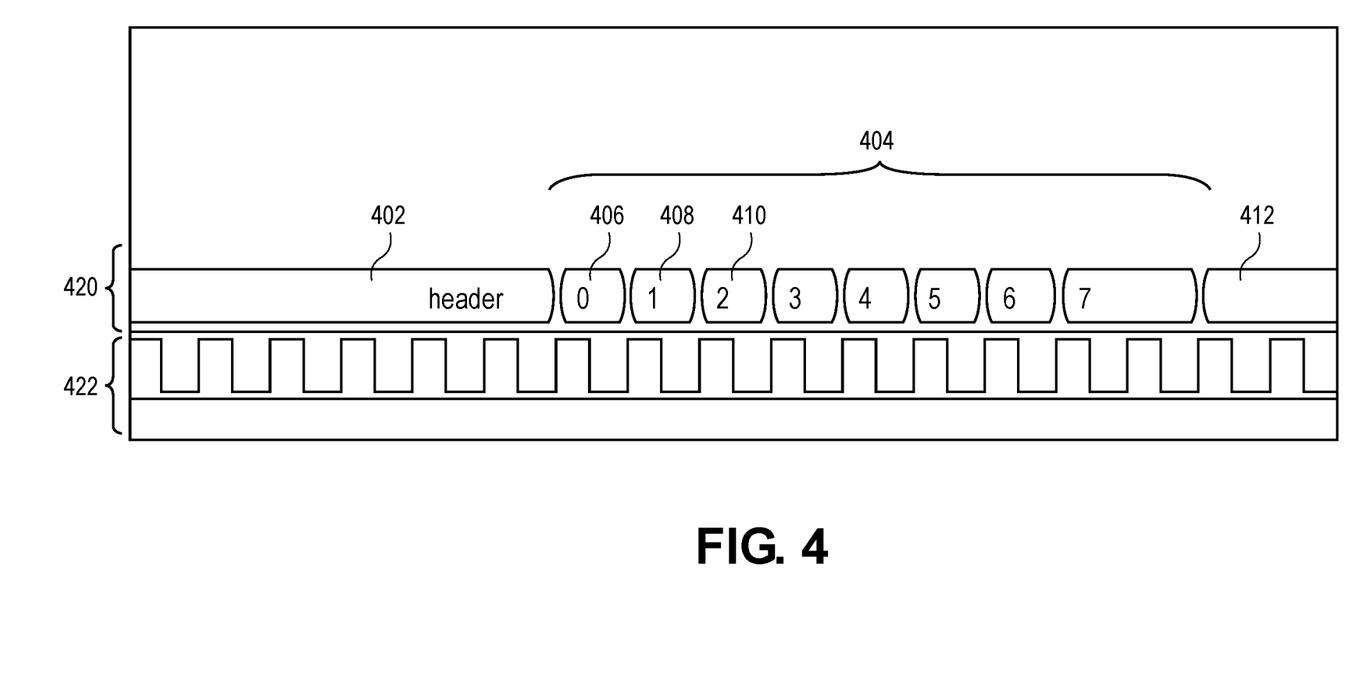
FIG. 4 is a data packet architecture used to implement the embodiments described herein.

FIG. 4 shows an example packet structure 420 and clock timer 422 as described herein. Components of packet diagram in FIG. 4 shows a packet 420, clock 422, and in the packet a header 402, packet data 404 including data from each of the amplifiers 406, 408, 410 etc. and a header for the next packet 412.

The packet 420 in the example of FIG. 4 includes a header 402, and eight rows of data 404 with a trailer 412. In this example, a packet is made up of a 10 bit word (on chip). The first word 402 is a header that includes a chip id or identifier. In some examples, chip id may be whether the chip is number 0,1,2,3 in a four chip example network. The chip id would be dependent upon the number of chips in the network.

An example header may be organized as:

| Word | Bits | Size | Name | Value | Notes |
|---|---|---|---|---|---|
| 0 | 3:0 | 4 | Chip ID | 0-15 | May be set to distinguish packets in MultiChip |
| 0 | 6:4 | 3 | Type | 0 or 1 | 0->ADC sample, 1->compression |
| 0 | 9:7 | 3 | Col addr | 0 or 7 | Specifies the column |

Data compression for examples using voltage spike detection instead of high bandwidth modes may be organized as:

| Word | Bits | Size | Name | Value | Notes |
|---|---|---|---|---|---|
| 1 | 7:0 | 8 | Spike events | 0-255 | spike event for row x when bit x = 1 |

For example the compression word "00001001" may correspond to spike events occurring in row 0 and 3. Typically only a single spike event will occur in a packet due to the sparsity of events. Packets on the debug port/full bandwidth stream may not have a header and are always 80 bits, representing the raw data for 8 rows at a time. In this example, the column addresses are implicit, as the columns come out in a deterministic order from 0 to 7.

In some examples, a packet type 406 may be included in the packet 420 and the type indicates whether the packet contains data in a compressed format or from a high bandwidth sampling arrangement. In some examples, subsequent words 406, 408, 410, etc. in the packet may be voltage readings from the amplifier rows themselves. In such examples, the number of words corresponds to the number of amplifier data that are included in the particular packet. In some examples, the subsequent words 406, 408, 410, may be summary data for compression events, sent by the compression engine. Once off chip, the packets may be further serialized. In some examples, the chip id may be 4 bits, the packet type may be 3 bits, and the column address may be 3 bits, for example. In the example, 412 is the header for the subsequent packet.

Figure 5:
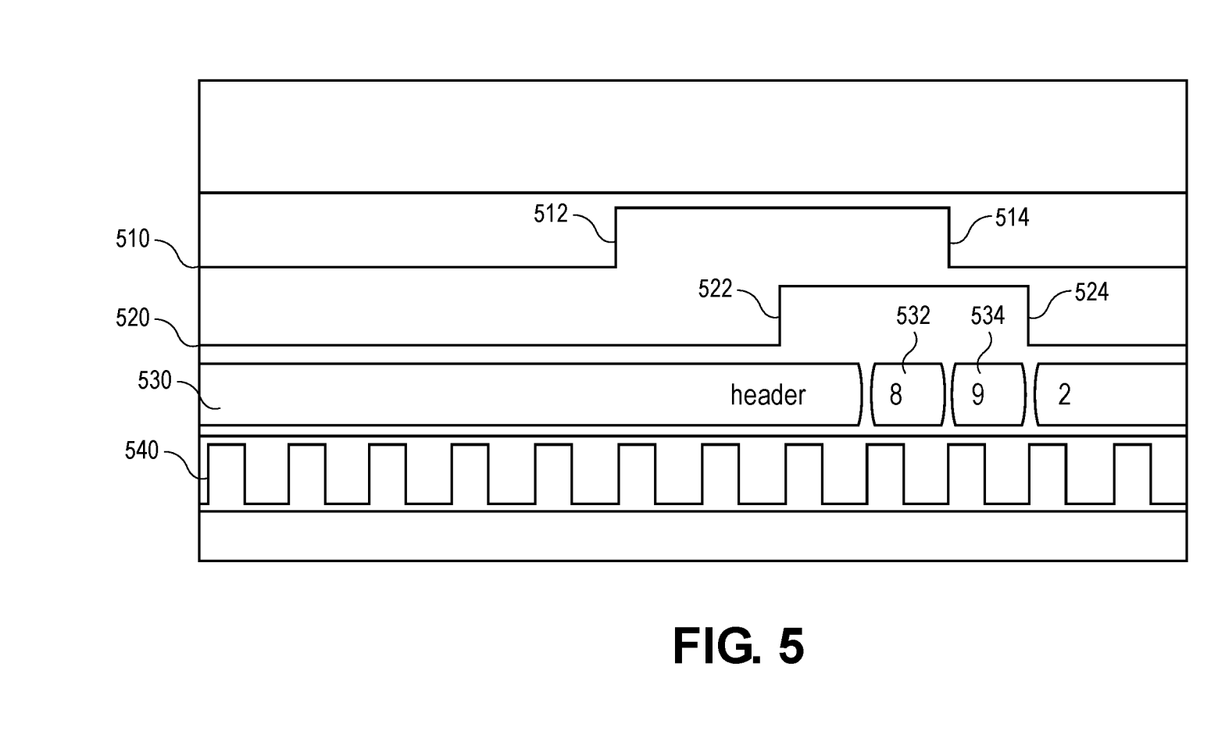
FIG. 5 is another data packet architecture used to implement the embodiments described herein.

Additional or alternative variable packet examples are shown in FIG. 5. FIG. 5 shows an example compressed packet with only two data words 532, 534 instead of eight as in FIG. 4.

Components of packet diagram in FIG. 5 shows a command signal 510 going high 512, and low 514, a receive signal 520, going high 522, and low 524, a packet header 530, packet data 532, 534, and a clock 540.

FIG. 5 also shows an example signal sequence for packet transfer between and among the component parts of the chip such as but not limited to the controller, merge circuitry, serializer, de-serializer, etc. In such communications, request signal 510 may indicate a packet is being requested 512 when the signal goes high. The ready to receive signal 520 may then indicate that the receiver is ready to receive a packet 522 when it goes high. The data in the packet includes a header 530 and data from the amplifier rows 532, 534. The request signal 510 then indicates that the packet has been sent 514 when the signal goes low The ready to receive signal 520 indicates it is no longer ready to receive 524 data when the signal goes low. The clock data 540 is also shown in the figure. Since the system can support more bandwidth than this specific chip is requesting, this means that the un-used bandwidth can be allocated to other chips.

Skip Channel Mode Examples

When determining which signals to pass on, in some examples, all rows in a column are read out every 160 kHz. For each column read, the controller would then build a packet based on information set in config circuitry. For example, if only two rows in a particular column are requested, the packet would consist of a header (10 bits)+the analog-to-digital converter data for those requested two rows (20 bits) for a 20 bit packet. In some example embodiments, a 30 bit packet may be implemented.

In this mode, each of the 64 channels may be configured to be skipped or sent determined by the 64 bit vector SkipVec. In such examples, SkipVec may refer to the mathematical vector instruction for the amplifier to pass event data. For example, channel n is skipped if the nth entry of SkipVec is set to 1, i.e, SkipVec[n]=1. For example, if column 1 is being processed by the controller, and SkipVec[15:8]=00110011, the resulting packet would be (assuming chip id 2 and ADC data=0 for all rows):

| Word | Binary msb-lsb | Notes |
|---|---|---|
| 0 | 0010000010 | col = 1, type = 0, id = 2 |
| 1 | 0000000000 | data for row 2 |
| 2 | 0000000000 | data for row 3 |
| 3 | 0000000000 | data for row 6 |
| 4 | 0000000000 | data for row 7 |

Note that this packet does not carry information about the origin of row data (e.g., word 1 is for row 2). To interpret row data, the receiver must also know SkipVec.

Skip Column Mode Examples

In a scheduled column mode example, for each amplifier column read, the controller may check the particular time step (1 of 8 then repeats) and decide whether to send the entire column based on what the config circuitry instructs. This arrangement allows fine control of which columns are sent on which time steps (for sub sampling) and across inter chip data passing. In some examples, all the row data is sent in this mode, which is the most efficient use of bandwidth by amortizing the header information. In some examples, additional data could be stored to skip rows in this mode.

In this mode, for example, each of the 8 columns in the amplifier array may be configured to be skipped or sent based on an 8×8 array SkipCol, indexed by col number and a time step that ranges from 0 to 7. In such examples, SkipCol may refer to the mathematical vector instruction for the amplifier to pass event data. Let t be an integer representing absolute time, and k=t %8. Then we skip column n at step k if SkipCol[n,k]=1.

For example, if SkipCol[7:0,3]=11001100, this corresponds to columns 0, 1, 3, and 4 being sent on time steps 3, 11, 19, . . . . These same columns might also be sent on other time steps as well.

In some examples, sending an entire column may be more efficient than sending subsets of a column, in cases where the overhead for the header word is amortized (10 bit header for 80 bits of data).

Customized Examples

As discussed, any combination of parameters such as but not limited to voltage thresholds and selective amplifier sampling may be used to identify and analyze neurological events as captured by the various electrodes. In some examples, chips and amplifiers may be separately analyzed in order to customize, change, and selectively change these parameters by reprogramming each chip. Such customization may be changed and/or updated as the chips are in operation. Such a customizable chip arrangement may allow users to calibrate the chips and only sample data coming from specific neurons, at certain thresholds, at different times as well as sample different electrodes at different times.

Customization may occur for each electrode differently and independently. Thus, analysis may occur for a specific set of the data from specific amplifiers, and later, a chip's compression engine may be programmed to sample a different set of the amplifiers than the first set. This may allow a titration of the high fidelity information with compressed data to allow a snapshot of a calibration curve.

Additionally or alternatively, event thresholds may be changed and/or updated, such as signal deviation may be changed between samples. This allows for different data to be captured, without much difference between sample times.

Additionally or alternatively, chip parameters may be configured on-the-fly to help visualize the effects of different parameters from the user's perspectives in real-time. This is due to the re-programmability of the chips at any time, as described. Additionally or alternatively, scan-chain may be used to set these parameters at the chip level. In some examples, this information or instruction may be passed along from chip-to-chip in a daisy-chain fashion on the network, understanding that with more chips networked in series, the programming may be passed slower as it makes its way from chip to chip down the network.

Additionally or alternatively, the systems and methods here may be used to visualize or calibrate whether the various voltage thresholds are set correctly to detect relevant voltage spikes. This may be accomplished by a combination of the features described herein, such as the ability to re-program chips, receive periodic summary information, change sample rates, change thresholds, and analyze individual amplifiers, or groups of amplifiers. For example, the system may even be customized to alternate between sending high-bandwidth data and outputs of the compression engine which arc lower bandwidth, and event driven data, or any combination of these.

Traffic Control Metering Examples

Another scenario is a high bandwidth example, one in which the various electrodes are producing and sending so many signals, that each chip is passing many packets to the next chip in a multi-chip network. Referring back to FIG. 1B, this would be a first chip 102 sending packets to the next chip 104, and so on. Such an arrangement may require more bandwidth. For example, scenarios where all of the signals are being processed from the electrodes, and/or the electrodes are sending data at fixed intervals. The number of voltage readings from the electrodes may be 20,000 times a second, in some high bandwidth examples.

In this serial arrangement, packet traffic may become congested as they are passed from one chip 102 to the next 104 and so on 106, 108. In such an example, with many packets being processed, if each chip 102, merely passed on all the packets as they were received, the data flow off the chip set 132 to the computer for storage and processing may be biased toward the closest chip 108, especially if a 50-50 arrangement were established between chips. In other words, if equal number of packets are being passed from the first chip 102 to the second 104, the packets passed to the third chip would be about 50% from chip 1 and about 50% from chip 2. But the packets passed to the fourth chip might be only 25% from chip 1 and 25% from chip 2 with 50% from chip 3. And with the fourth chip, it may be 12.5% from chip 1, 102, 12.5% from chip 2, 104 and 25% from chip 3, 106 with 50% from chip 4 108. This would unfairly bias the packet flow to the nearer chips to the computer and create an imbalance of data.

One way to solve this biasing problem would be to meter the packets from each chip to offset this bias. In such examples, when the packets are passed from the second chip, 104 to the third chip, 106, the number of packets from the third chip, 106 are not passed with 50% of the bandwidth, rather, they are passed with only 33% of the bandwidth and those from the first chip, 102 and second chip, 104 are passed with 66% of the bandwidth. This arrangement would allow for equal number of packets from each of the first three chips to be passed to the fourth chip 108. Finally, in this four chip arrangement of FIG. 1B, the fourth chip 132, nearest the computer offload 132 would only use 25% of the bandwidth, thus biasing the first 102, second 104, and third chips 106 so that bandwidth was equally shared.

The individual merge circuitry components in each chip may be programmed with these metering instructions to create these balanced data packet scenarios. In some examples, the buffers in the serializer and/or deserializer may also be instructed to aid the merge circuitry in this balancing act or meter the packets it is passing along as well.

Pin Out Examples

Below is an example pin out for the 64 channels and additional channels.

| Name | Type | 110 | Notes |
| --- | --- | --- | --- |
| li_req | digital | in | Request for Li (left in) port, indicates packet ready to be sent |
| li_data | digital | in | Data for Li (left in) port, latch on negedge of clock after selected |
| li_sel | digital | out | Select for Li (left in) port, to initiate data transfer |
| ro_req | digital | out | Request for Ro (right in) port, indicates packet ready to be sent |
| ro_data | digital | out | Data for Ro (right out), sent on posedge of clock after selected |
| ro_sel | digital | in | Select for Ro (right out), to initiate data transfer |
| cnv_ro_req | digital | out | Request for Debug port, indicates packet ready |
| cnv_ro_data | digital | out | Data for Debug port, sent on posedge of clock |
| rst | digital | in | Asynchronous reset for all logic on chip, including configuration |
| clk | digital | in | Clock signal for Li, Ro, and Dbg ports, nominally 15.360 MHz |
| scan_din | digital | in | Scan data input for chip configuration |
| scan_dout | digital | out | Scan data output |
| scan_clk | digital | in | Scan clock, nominally < 5 MHz |
| scan_en | digital | in | Scan enable for latching data |
| adc_en | digital | in | Enable (active high) for on chip network, also can be set by scan |

-continued

| Name | Type | 110 | Notes |
|---|---|---|---|
| dbg_en | digital | in | Enable (active high) for debug port, also can be set by scan |
| neo_en | digital | in | Enable (active high) for compression, also can be set by scan |
| reg_disable | digital | in | Enable (active high) to disable regulator |
| scan_dbg_pass | digital | in | Extra mode for multi chip scan mode, currently unused, set to gnd |
| mchip_scan_cfg | digital | in | Extra mode for multi chip scan mode, currently unused, set to gnd |
| ch0 to ch63 | analog | in | Input to differential amplifier, note ch0 is bottom left and ch63 is top right |
| ref | analog | in | Common ref input to all differential amplifiers |
| vdd500 | analog | out | Probe voltage for ADC |
| vref | analog | out | Probe for vref |
| avdd | power | in/out | Analog vdd, set by internal LDO. Can be overridden when reg disable is high |
| dvdd | power | in/out | Digital vdd, set by internal LDO. Can be overridden when reg disable is high |
| vunreg | power | in | Unregulated vdd, nominally 1.8 V |
| vpad | power | in | Pad vdd, nominally 1.8 V |
| gnd | power | in | Shared ground |
| dummy | n/a | n/a | For mechanical stability |

The foregoing description, for purpose of explanation, has been described with reference to specific embodiments. However, the illustrative discussions above are not intended to be exhaustive or to limit the invention to the precise forms disclosed. Many modification s and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

The innovations herein may be implemented via one or more components, systems, servers, appliances, other subcomponent s, or distributed between such elements. When implemented as a system, such systems may include an/or involve, inter aha, components such as software modules, general-purpose CPU, RAM, etc. found in general-purpose computers. In implementations where the innovations reside on a server, such a server may include or involve components such as CPU, RAM, etc., such as those found in general-purpose computers.

Additionally, the innovations herein may be achieved via implementations with disparate or entirely different software, hardware and/or firmware components, beyond that set forth above. With regard to such other components (e.g., software, processing components, etc.) and/or computer-readable media associated with or embodying the present inventions, for example, aspects of the innovations herein may be implemented consistent with numerous general purpose or special purpose computing systems or configurations. Various exemplary computing systems, environments, and/or configurations that may be suitable for use with the innovations herein may include, but are not limited to: software or other components within or embodied on personal computers, servers or server computing devices such as routing/connectivity components, hand-held or laptop devices, multiprocessor systems, microprocessor-based systems, set top boxes, consumer electronic devices, network PCs, other existing computer platforms, distributed computing environments that include one or more of the above systems or devices, etc.

In some instances, aspects of the innovations herein may be achieved via or performed by logic and/or logic instructions including program modules, executed in association with such components or circuitry, for example. In general, program modules may include routines, programs, objects, components, data structures, etc. that performs particular tasks or implement particular instructions herein. The inventions may also be practiced in the context of distributed software, computer, or circuit settings where circuitry is connected via communication buses, circuitry or links. In distributed settings, control/instructions may occur from both local and remote computer storage media including memory storage devices.

Innovative software, circuitry and components herein may also include and/or utilize one or more type of computer readable media. Computer readable media can be any available media that is resident on, associable with, or can be accessed by such circuits and/or computing components. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic tape, magnetic disk storage or other magnetic storage devices, or any other medium which can be used to store the desired information and can accessed by computing component. Communication media may comprise computer readable instructions, data structures, program modules and/ or other components. Further, communication media may include wired media such as a wired network or direct-wired connection, however no media of any such type herein includes transitory media. Combinations of the any of the above are also included within the scope of computer readable media.

In the present description, the terms component, module, device, etc. may refer to any type of logical or functional software elements, circuits, circuitry and/or processes that may be implemented in a variety of ways. For example, the functions of various circuits and/or circuitry can be combined with one another into any other number of modules. Each module may even be implemented as a software program stored on a tangible memory (e.g., random access memory, read only memory, CD-ROM memory, hard disk drive, etc.) to be read by a central processing unit to implement the functions of the innovations herein. Or, the modules can comprise programming instruction s transmitted to a general purpose computer or to processing/graphics hardware via a transmission carrier wave. Also, the modules can be implemented as hardware logic circuitry implementing the functions encompassed by the innovations herein. Finally, the modules can be implemented using special purpose instructions (SIMD instructions), field programmable logic arrays or any mix thereof which provides the desired level performance and cost.

As disclosed herein, features consistent with the present inventions may be implemented via computer-hardware, software and/or firmware. For example, the network systems and methods disclosed herein may be embodied in various forms including, for example, a data processor, such as a computer that also includes a database, digital electronic circuitry, firmware, software, or in combinations of them. Further, while some of the disclosed implementations describe specific hardware components, systems and methods consistent with the innovations herein may be implemented with any combination of hardware, software and/or firmware. Moreover, the above-noted features and other aspects and principles of the innovations herein may be implemented in various environments. Such environments and related applications may be specially constructed for performing the various routines, processes and/or operations according to the invention or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the invention, or it may be more convenient to construct a specialized apparatus or system to perform the required methods and techniques.

Aspects of the method and system described herein, such as the logic, may also be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some possibilities for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy (neural) logic, quantum devices, and hybrids of any of the above device types. The underlying device technologies may be provided in a variety of component types, e.g., metal-oxide semiconductor field-effect transistor ("MOSFET") technologies like complementary metal-oxide semiconductor ("CMOS"), bipolar technologies like emitter-coupled logic ("ECL"), polymer technologies (e.g., silicon-conjugated polymer and metal-conjugated polymer-metal structures), mixed analog and digital, and so on.

It should also be noted that the various logic and/or functions disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) though again does not include transitory media. Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Although certain presently preferred implementations of the invention have been specifically described herein, it will be apparent to those skilled in the art to which the invention pertains that variations and modifications of the various implementations shown and described herein may be made without departing from the spirit and scope of the invention. Accordingly, it is intended that the invention be limited only to the extent required by the applicable rules of law.

What is claimed is:

1. A system, comprising, a chip including,
    an array of amplifiers, each amplifier in the array in communication with an electrode configured to receive neurological voltage signals;
    an analog-to-digital converter, configured between the array of amplifiers and a controller, the analog-to-digital converter configured to convert analog signals from the array of amplifiers to digital signals, the controller configured to instruct the analog-to-digital converter to pass only signals from certain rows of amplifiers in the array of amplifiers;
    a multiplexer, configured between the analog-to-digital converter and the controller, the multiplexer configured to serialize the digitized amplified neurological voltage signals and pass the serialized digitized amplified neurological voltage signals to the controller, the controller further configured to instruct the multiplexer to pass only signals from certain columns of amplifiers in the array of amplifiers;
    a configuration circuitry in communication with the array of amplifiers and the controller, the configuration circuitry configured to receive program instructions and instruct the amplifiers of a voltage threshold and instruct the controller to pass on signals from only specific rows and columns of amplifiers corresponding to a neurological voltage signal exceeding the voltage threshold;
    the controller in communication with the array of amplifiers, the controller further configured to packetize the neurological voltage signals into data packets, wherein the data packets are variable in length depending on a number of amplifiers instructed by the controller to be passed on;
    a compression engine in communication with the controller, the compression engine configured to compress data packets from the controller and pass the compressed data packets to a merge circuitry; and the merge circuitry configured to receive the compressed data packets from the compression engine and pass the packetized voltage signals off the chip.

2. The system of claim 1 wherein the configuration circuitry is further configured to instruct the compression engine to send summary data to the merge circuitry.

3. The system of claim 1 wherein the merge circuitry is configured to pass data packets to a second chip, in communication with the chip in serial.

4. The system of claim 3 wherein the merge circuitry passes data packets to the second chip through a serializer queue.

5. The system of claim 1 wherein the configuration circuitry is configured to instruct the amplifiers of a voltage threshold that is individualized for specific amplifiers in the array of amplifiers.

6. A method, comprising,
receiving neurological voltage signals at an array of amplifiers on a chip, the neurological voltage signals received through at least one electrode;
converting, by an analog-to-digital converter, the neurological voltage signals to digital signals;
instructing the analog-to-digital converter, by a controller on the chip, to pass only signals from certain rows of amplifiers in the array of amplifiers;
serializing, by a multiplexer on the chip, the digitized amplified neurological voltage signals and passing the serialized digitized amplified neurological voltage signals to the controller;
instructing the multiplexer, by the controller, to pass only signals from certain columns of amplifiers in the array of amplifiers;
sending instructions by a configuration circuitry on the chip, to the controller on the chip, the instructions including instructions to pass on signals from only specific columns and rows of amplifiers in the amplifier array corresponding to a neurological voltage signal exceeding a voltage threshold;
packetizing, at the controller, the passed on signals from the array of amplifiers;
wherein the packets are variable in length depending on a number of amplifiers passing on signals;
compressing the packets from the controller, by a compression engine in communication with the controller and a merge circuitry;
passing the compressed packets to the merge circuitry, by the compression engine; and
passing the packets off the chip, by the merge circuitry, the merge circuitry further in communication with the controller.

7. The method of claim 6 further comprising, sending instruction, by the configuration circuitry, to the compression engine to send summary data to the merge circuitry.

8. The method of claim 6 further comprising, passing, by the merge circuitry, data packets to a second chip, in communication with the chip in serial.

9. The method of claim 8 wherein, the passing, by the merge circuitry, of data packets to the second chip is through a serializer queue.

10. A non-transitory computer readable media for a method of handling data, the method comprising,
receiving neurological voltage signals at an array of amplifiers on a chip, the neurological voltage signals received through at least one electrode;
converting, by an analog-to-digital converter, the neurological voltage signals to digital signals;
instructing the analog-to-digital converter, by a controller on the chip, to pass only signals from certain rows of amplifiers in the array of amplifiers;
serializing, by a multiplexer on the chip, the digitized amplified neurological voltage signals and passing the serialized digitized amplified neurological voltage signals to the controller;
instructing the multiplexer, by the controller, to pass only signals from certain columns of amplifiers in the array of amplifiers;
sending instructions by a configuration circuitry on the chip, to the controller on the chip, the instructions including instructions to pass on signals from only specific columns and rows of amplifiers in the amplifier array;
packetizing, at the controller, the passed on signals from the array of amplifiers;
wherein the packets are variable in length depending on a number of amplifiers passing on signals;
compressing the packets from the controller, by a compression engine in communication with the controller and a merge circuitry, based a neurological voltage signal exceeding a voltage threshold instructed by the configuration circuitry;
passing the compressed packets to the merge circuitry, by the compression engine; and
passing the packets off the chip, by the merge circuitry, the merge circuitry further in communication with the controller.

11. The non-transitory computer readable media of claim 10 further comprising,
sending instruction, by the configuration circuitry, to the compression engine to send summary data to the merge circuitry.

12. The non-transitory computer readable media of claim 10 further comprising, passing, by the merge circuitry, data packets to a second chip, in communication with the chip in serial.

13. The non-transitory computer readable media of claim 12 wherein, the passing, by the merge circuitry, of data packets to the second chip is through a serializer queue.

14. The method of claim 6 wherein the configuration circuitry is configured to instruct the amplifiers of a voltage threshold that is individualized for specific amplifiers in the array of amplifiers.

15. The system of claim 1 wherein the voltage threshold corresponds to a characteristic neural spike voltage.

16. The method of claim 6 wherein the voltage threshold corresponds to a characteristic neural spike voltage.

17. The non-transitory computer readable media of claim 12 wherein the voltage threshold corresponds to a characteristic neural spike voltage.

* * * * *